US00PP25143P2

(12) United States Plant Patent
Smith

(10) Patent No.: US PP25,143 P2
(45) Date of Patent: Dec. 2, 2014

(54) ***CHRYSANTHEMUM* PLANT NAMED 'CIFZ0010'**

(50) Latin Name: *Chrysanthemum×morifolium*
Varietal Denomination: CIFZ0010

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 126 days.

(21) Appl. No.: 13/815,222

(22) Filed: Feb. 11, 2013

(51) Int. Cl.
*A01H 5/00* (2006.01)

(52) U.S. Cl.
USPC ..... Plt./286

(58) Field of Classification Search
USPC ..... Plt./286, 297
See application file for complete search history.

*Primary Examiner* — Kent L Bell
(74) *Attorney, Agent, or Firm* — Joshua L. Price

(57) ABSTRACT

A new *Chrysanthemum* plant named 'CIFZ0010' particularly distinguished by the small duplex-type inflorescences with red-purple colored ray florets, medium yellow-green foliage, medium-sized and very rounded ball-like plant habit with a mid-October natural flowering season response.

1 Drawing Sheet

Latin name of the genus and species of the plant claimed: *Chrysanthemum×morifolium.*

Varietal denomination: 'CIFZ0010'.

BACKGROUND OF THE NEW PLANT

The present invention comprises a new *Chrysanthemum*, botanically known as *Chrysanthemum×morifolium*, and hereinafter referred to by the variety name 'CIFZ0010'.

'CIFZ0010' is a product of a planned breeding program. The new cultivar has small duplex-type inflorescences with red-purple colored ray florets, medium yellow-green foliage, medium-sized and very rounded ball-like plant habit with a mid-October natural flowering season response.

'CIFZ0010' originates as a natural whole plant mutation of a purple duplex type parent named '07-M322'. 'CIFZ0010' was discovered and selected by the inventor as a single flowering plant within a large population of the parent cultivar grown in a greenhouse in Gilroy, Calif. in March 2010. The parent cultivar '07-M322' has a little larger overall size and a bit slower natural season flowering response.

The first act of asexual reproduction of 'CIFZ0010' was accomplished when vegetative cuttings were propagated from the initial selection in April 2010 in a greenhouse in Gilroy, Calif.

BRIEF SUMMARY OF INVENTION

Horticultural examination of plants grown from cuttings of the plant initiated in April 2010, and continuing thereafter, has demonstrated that the combination of characteristics as herein disclosed for 'CIFZ0010' are firmly fixed and are retained through successive generations of asexual reproduction.

'CIFZ0010' has not been observed under all possible environmental conditions. The phenotype may vary significantly with variations in environment such as temperature, light intensity and day length.

Plant Breeder's Rights for this cultivar were applied for in Canada on Feb. 24, 2012 (12-7529) and at the Community Plant Variety Office on May 10, 2012 (2012/1027). 'CIFZ0010' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0010' with colors being as true as possible with an illustration of this type. The photographic drawing shows three flowering plants of the new variety growing together in one container and a close-up of the inflorescence.

DETAILED BOTANICAL DESCRIPTION

The plant descriptions, measurements and aforementioned photographs were taken outdoors in Gilroy, Calif. in early January 2013. These plants were approximately 22 weeks of age. The plants were grown originally as stock plants for production, and then allowed to flower out for these descriptions and photographs. The plants had been terminally pinched several times through this production period before flowering.

Color references are made to The Royal Horticultural Society Colour Chart (R.H.S.) 2001.

TABLE 1

DIFFERENCES BETWEEN THE NEW VARIETY 'CIFZ0010' AND A MOST SIMILAR VARIETY

| | 'CIFZ0010' | 'Yobarbie' (U.S. Plant Pat. No. 17,008) |
|---|---|---|
| Inflorescence color: | Darker/more purple | Lighter purple |
| Quantity of disc florets: | More | Fewer |
| Plant habit: | Rounder | Less round |
| Blackcloth flowering response: | About 5 days faster | About 5 days slower |
| Natural season response: | About 1 week faster | About 1 week slower |

Plant:

*Form, growth and habit.*—Herbaceous garden-type, stems upright and freely branching.

*Plant height.*—26-28.0 cm.

*Plant height* (*inflorescence included*).—32-35.0 cm.

*Plant width.*—About 30.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—Lighter than RHS 147A. Lower surface: Closest to RHS 147B.

*Mature, leaf color, upper surface.*—Closest to RHS 147A. Lower surface: Closest to RHS147B.

*Length.*—2.6-4.5 cm.

*Width.*—2.7-3.0 cm.

*Shape.*—Stocky-ovate to ovate.

*Base shape.*—Attenuate.

*Apex shape.*—Mucronulate.

*Margin.*—Slightly palmately lobed to irregularly incised; dentate.

*Texture, upper surface.*—Bifid T-shaped hairs.

*Texture, lower surface.*—Bifid T-shaped hairs.

*Color of veins, upper surface.*—Closest to RHS 147A.

*Color of veins, lower surface.*—Closest to RHS 147B.

*Pattern of veining.*—Palmate.

*Petiole color.*—RHS 147A to RHS 147B.

*Length.*—1-1.2 cm.

*Diameter.*—0.1-0.15 cm.

*Texture.*—Bifid T-shaped hairs.

Stem:

*Quantity of main branches per plant.*—6-8.

*Color of stem.*—Closest to RHS 146A.

*Length of stem.*—20-25.0 cm.

*Diameter.*—0.2-0.25 cm.

*Length of internodes.*—1.5-2.5 cm.

*Texture.*—Bifid T-shaped hairs.

*Color of peduncle.*—Closest to RHS 144A.

*Length of peduncle.*—2.5-3.5 cm.

*Peduncle diameter.*—0.075 cm.

*Texture.*—Bifid T-shaped hairs.

Inflorescence:

*Type.*—Compositae, solitary duplex-type, inflorescences borne terminally above foliage, ray florets arranged acropetally on a capitulum.

*Quantity of short days to flowering* (*response time*).—About 7.5 weeks.

*Natural season flowering.*—Mid-October.

*Quantity of inflorescences per plant.*—About 75, plus about 80 buds.

*Lastingness of individual blooms on the plant.*—About 4 weeks from first color.

*Fragrance.*—Slightly spicy.

Bud (just when opening/showing color):

*Color.*—Closest to RHS N186D.

*Length.*—0.8-1.1 cm.

*Width.*—0.6-0.7 cm.

*Shape.*—Oblate.

Immature inflorescence:

*Diameter.*—2.9-3.4 cm.

*Color of ray florets, upper surface.*—Closest to RHS N186D.

*Color of ray florets, lower surface.*—Lighter than RHS 71A.

Mature inflorescence:

*Diameter.*—3.8-4.0 cm naturally; 4.0-4.2 cm flattened out.

*Depth.—About* 1.5 cm.

*Total diameter of disc.*—0.5-0.7 cm.

*Receptacle color.*—RHS 145C.

*Receptacle height.*—0.2 cm.

*Receptacle diameter.*—0.2 cm.

Ray florets:

*Average quantity of florets.*—50 in 4-5 whorls.

*Color of florets, upper surface.*—Closest to but lighter than RHS 71A.

*Color of florets, lower surface.*—Lighter than RHS 70A.

*Length.*—1.6-1.8 cm.

*Width.*—0.3-0.45 cm.

*Shape.*—Oblong.

*Apex shape.*—Mucronulate.

*Base shape.*—Cuneate.

*Margin.*—Entire.

*Texture, upper surface.*—Papillose.

*Texture, lower surface.*—Papillose.

Disc florets:

*Average quantity of florets.*—30-40.

*Color of florets.*—RHS 1D with RHS 7A apex.

*Length.*—0.45 cm.

*Width.*—0.1 cm.

*Shape.*—Tubular, elongated.

*Apex shape.*—Acute, 5 pointed.

*Texture, inner surface.*—Glabrous.

*Texture, outer surface.*—Glabrous.

Phyllaries:

*Quantity.*—40-45.

*Color, upper surface.*—RHS 138A.

*Color, lower surface.*—RHS 138B.

*Length.*—0.4-0.6 cm.

*Width.*—0.1 cm.

*Shape.*—Lanceolate.

*Apex shape.*—Acute.

*Base.*—Fused.

*Margins.*—Entire.

*Texture, upper surface.*—Glabrous.

*Texture, lower surface.*—Bifid T-shaped hairs.

Reproductive organs:

*Pistil.*—1, found on both types of florets.

*Length.*—1.0 cm.

*Style color.*—Greener than RHS 1B.

*Style length.*—0.9 cm.

*Stigma color.*—RHS 6C.

*Stigma shape*.—Bi-parted.
*Ovary*.—Not sufficiently developed to measure and describe.
*Stamens*.—4, found only on the disc florets.
*Color of filaments*.—Greener than RHS 1B.
*Length filaments*.—0.1 cm.
*Anther color*.—RHS 6C.
*Anther length*.—0.1 cm.
*Anther shape*.—Oblong.
*Color of pollen*.—RHS 9B.
*Pollen amount*.—Normal.
*Fertility/seed set*.—Has not been observed to date.
*Disease/pest resistance*.—Has not been observed to date.

What is claimed is:

1. A new and distinct variety of *Chrysanthemum* plant named 'CIFZ0010' substantially as illustrated and described herein.

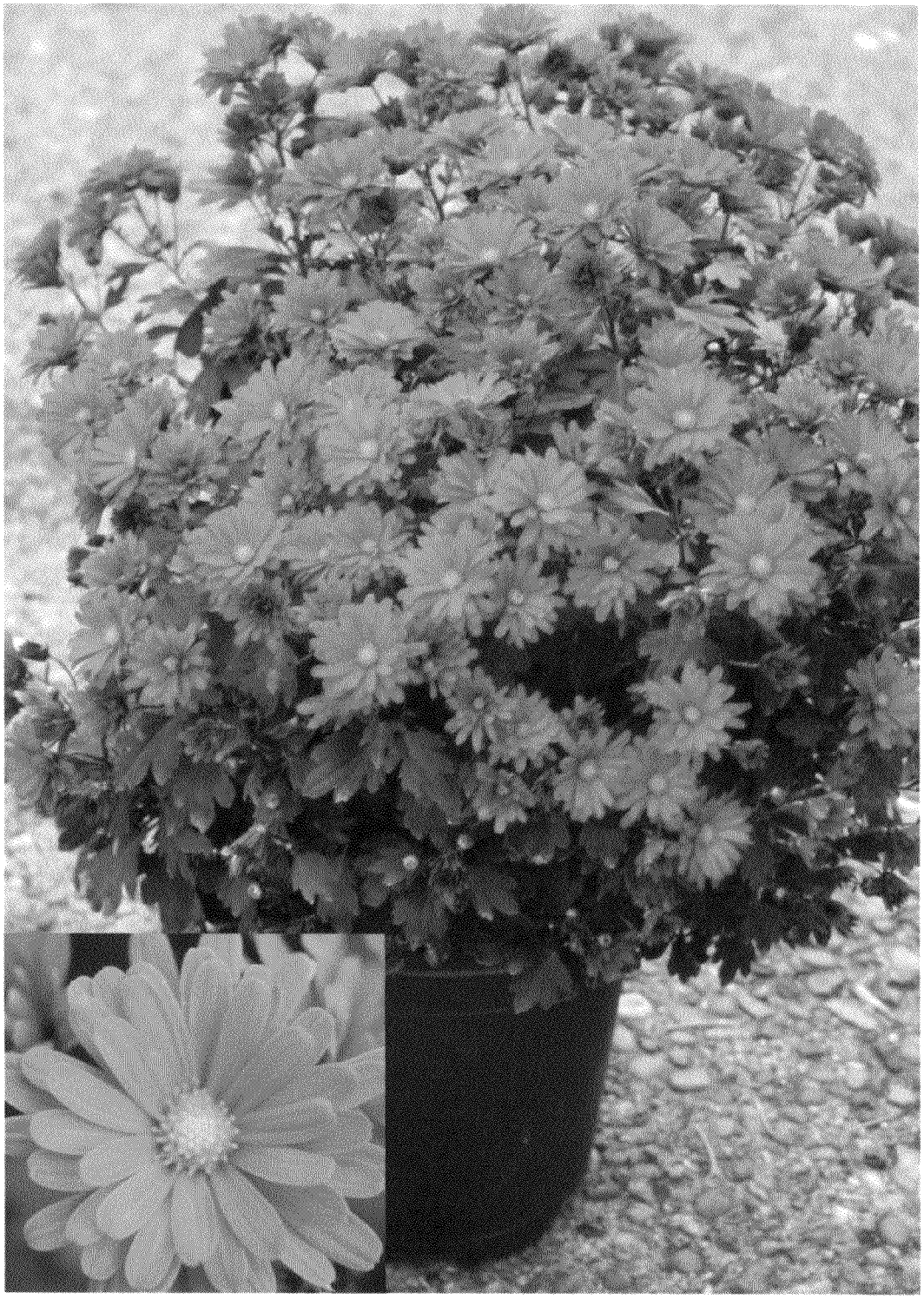

* * * * *